United States Patent
Aerni et al.

(10) Patent No.: US 9,594,777 B1
(45) Date of Patent: Mar. 14, 2017

(54) IN-DATABASE SINGLE-NUCLEOTIDE GENETIC VARIANT ANALYSIS

(71) Applicant: GoPivotal, Inc., San Mateo, CA (US)

(72) Inventors: Sarah J. Aerni, San Francisco, CA (US); Noelle L. Sio, Montclair, CA (US)

(73) Assignee: Pivotal Software, Inc., San Francisco, CA (US)

( * ) Notice: Subject to any disclaimer, the term of this patent is extended or adjusted under 35 U.S.C. 154(b) by 291 days.

(21) Appl. No.: 13/968,404

(22) Filed: Aug. 15, 2013

(51) Int. Cl.
*G06F 17/30* (2006.01)
*G06F 19/22* (2011.01)

(52) U.S. Cl.
CPC .. *G06F 17/30289* (2013.01); *G06F 17/30598* (2013.01); *G06F 19/22* (2013.01)

(58) Field of Classification Search
CPC ...... G06F 19/14; G06F 19/3481; G06F 19/22; G06F 19/24; G06F 17/30598
USPC ..... 702/19, 20; 707/707, 737, 739, 752, 754
See application file for complete search history.

(56) References Cited

U.S. PATENT DOCUMENTS

| | | | |
|---|---|---|---|
| 8,645,343 B2* | 2/2014 | Wong | G06F 19/22 702/20 |
| 2002/0133299 A1 | 9/2002 | Jacob et al. | |
| 2003/0165836 A1 | 9/2003 | Schork et al. | |
| 2004/0080536 A1* | 4/2004 | Yakhini | G06F 19/26 715/764 |
| 2005/0158788 A1 | 7/2005 | Schork et al. | |
| 2012/0102041 A1* | 4/2012 | Park | G06F 19/28 707/741 |
| 2014/0012843 A1* | 1/2014 | Soon-Shiong | G06F 19/18 707/736 |

* cited by examiner

*Primary Examiner* — Marc Filipczyk
(74) *Attorney, Agent, or Firm* — Fish & Richardson P.C.

(57) ABSTRACT

Genetic data in row-wise flat files, such as VCF and VCF-like files, comprising a plurality of data elements of different types is analyzed using a parallel framework in an MPP shared-nothing distributed database having a plurality of distributed segments by first parsing the data into groups of data elements of the same types, converting the data into entry-wise genetic data such that the same types of data elements are in a column, and distributing and storing the entry-wise genetic data in the distributed segments. SQL database queries are used to analyze the genetic data, including locating probable significant associations between genotype and phenotype data.

18 Claims, 7 Drawing Sheets

| Individual ID | SNP 1 | SNP 2 | | SNP 100 |
|---|---|---|---|---|
| 1 | AA | CC | | TA |
| 2 | AC | TC | | AT |
| N | TG | CA | | GG |

Figure 3A

| Individual | Covariates | | | | | SNP | |
|---|---|---|---|---|---|---|---|
| | Sex | Age | BMI | ID1 | ID 2 | | ID 1000000 |
| 1 | F | 23 | 18 | AA | CC | | TT |
| 2 | M | 39 | 41 | AT | CG | | TT |
| 3 | M | 50 | 23 | AA | GG | | TC |
| ... | | | | | | | |
| 270 | F | 19 | 24 | TT | CG | | TC |
| ... | | | | | | | |

Figure 3B

| SNP ID | Individual 1 | Individual 2 |
|---|---|---|
| 1 | AA | AC |
| 2 | CC | TC |
| 100 | TA | AA |

Figure 3C

| Individual ID | Characteristic | Value |
|---|---|---|
| 1 | Ethnicity | YRB |
| 1 | Sex | F |
| 1 | Age | 23 |
| 2 | Ethnicity | CEU |
| 2 | Sex | M |
| 2 | Age | 39 |

Figure 6

| Individual ID | SNP ID | Genotype Value |
|---|---|---|
| 1 | 1 | AA |
| 1 | 2 | CC |
| 1 | 100 | TA |
| 2 | 1 | AC |
| 2 | 2 | TC |
| 2 | 100 | AT |
| N | 1 | TG |
| N | 2 | CA |
| N | 100 | GG |

IN-DATABASE SINGLE-NUCLEOTIDE GENETIC VARIANT ANALYSIS

BACKGROUND

This invention relates generally to bioinformatics, and more particularly to improved methods for the rapid and efficient analysis of genetic variants in genomic data using a distributed parallel framework.

Analysis of DNA sequence data is becoming a common for research and diagnostics. A single-nucleotide polymorphism (SNP) is a DNA sequence variation occurring when a single nucleotide A, C, G, T, blank (which indicates a deletion), multiple loci, e.g., AC, AG, etc., in the genome at a particular location differ between individuals, e.g., humans. Variations in the DNA sequences (which we generally refer to as SNPs although these can be extended to other variants, including structural variants) of humans can affect how individuals develop diseases and respond to pathogens, chemicals, drugs and other agents. They are important for personalized medicine, and SNPs are used as in genome-wide association studies related to diseases and normal traits.

Processing of genetic data to identify associations, relations and possible anomalies is generally a resource-intensive and time-consuming process. There are about three billion base pairs in human DNA, some number of which may contain a variant, and generally it is necessary to look at each SNP in turn and compare it to other SNPs and to other samples to determine the probability of the variant being related to a particular disease or trait. There are many different ways in which genetic data can be represented and stored. For example, an individual's genetic data could be stored as a row in a flat file. The flat file may contain the genotypes in a predefined order for genetic markers. Each flat file may contain multiple rows of data for multiple SNPs for each individual. Other covariate or phenotype information related to an individual could be stored in the same file or in other files with identifiers allowing linking the genetic and other covariate data of an individual. In this version of flat file design, the SNPs must be in the same order for each individual. Another common and intuitive storage format is the variant cell format (VCF) or VCF-like formats. In these formats, each row contains data on a single SNP or variant. SNP data for multiple individuals may also be included on each line or row for a particular variant. In this document, VCF will refer to both strictly VCF and VCF-like formats. These formats may also contain additional information about SNPs, including quality scores and filters and can contain further rich information. In general, all the aforementioned flat files are stored in what we refer to as row-wise storage of SNP data.

Because of the vast amount of genetic data and the various forms in which it is available, processing of the data is very inefficient and resource intensive. Running comparisons across individuals may require that the row-wise flat file data first be extracted out of the format in which it is stored, merged with others or otherwise accessed independently. This must be repeated each time more data is added, and some steps repeated every time that a comparison is made, and is memory bound. It is a computationally heavy process and is a mandatory first step, regardless of the complexity of the comparison or analysis. For example, a simple count of allele distribution over a population stratified by some disease could require scanning multiple files and filtering using information derived from another location (for example on disease status). When looking at a comparison between two separate SNPs, for example, it could be necessary to scan through the data twice looking for the two separate SNPs, or building custom query or writing code to access a particular row or column depending on the way the data is represented. The data set may be very large, e.g., possibly 1,000,000 data items per individual, and scanning it is a very time-consuming and resource-intensive process. Although the process is inherently parallel in nature, as the identical operation is being performed across every individual, the row-wise data format is serial and it must be scanned repeatedly each time an additional individual or SNP is examined to locate items of interest. This inhibits the ability of researchers easily to conduct exploratory ad-hoc "what if" searches to look for correlations between a variety of different SNPs and different data items.

It is desirable to provide methods for enhancing the efficiency and reducing the time and resources required for processing genetic data, and it is to these ends that the present invention is directed.

BRIEF DESCRIPTION OF THE DRAWINGS

FIG. 3A is diagrammatic view of one row-wise flat file format for representing genetic data for multiple individuals;

FIG. 3B is a diagrammatic view of another row-wise flat file format similar to FIG. 3A that also includes covariate data;

FIG. 3C is a diagrammatic view showing an intuitive representation of a portion of the fields of a VCF-like row-wise flat file format for genetic data for multiple individuals;

FIG. 5 illustrates a entry-wise data model in accordance with the invention; and FIG. 6 illustrates a data model for covariate and phenotype data for use in the invention.

DESCRIPTION OF PREFERRED EMBODIMENTS

This invention is particularly well adapted to processing SNPs of human genomes and will be described in that context. It will be appreciated, however, that this is illustrative of only one utility of the invention and that invention is applicable to processing other types of genetic data.

Figure 1:
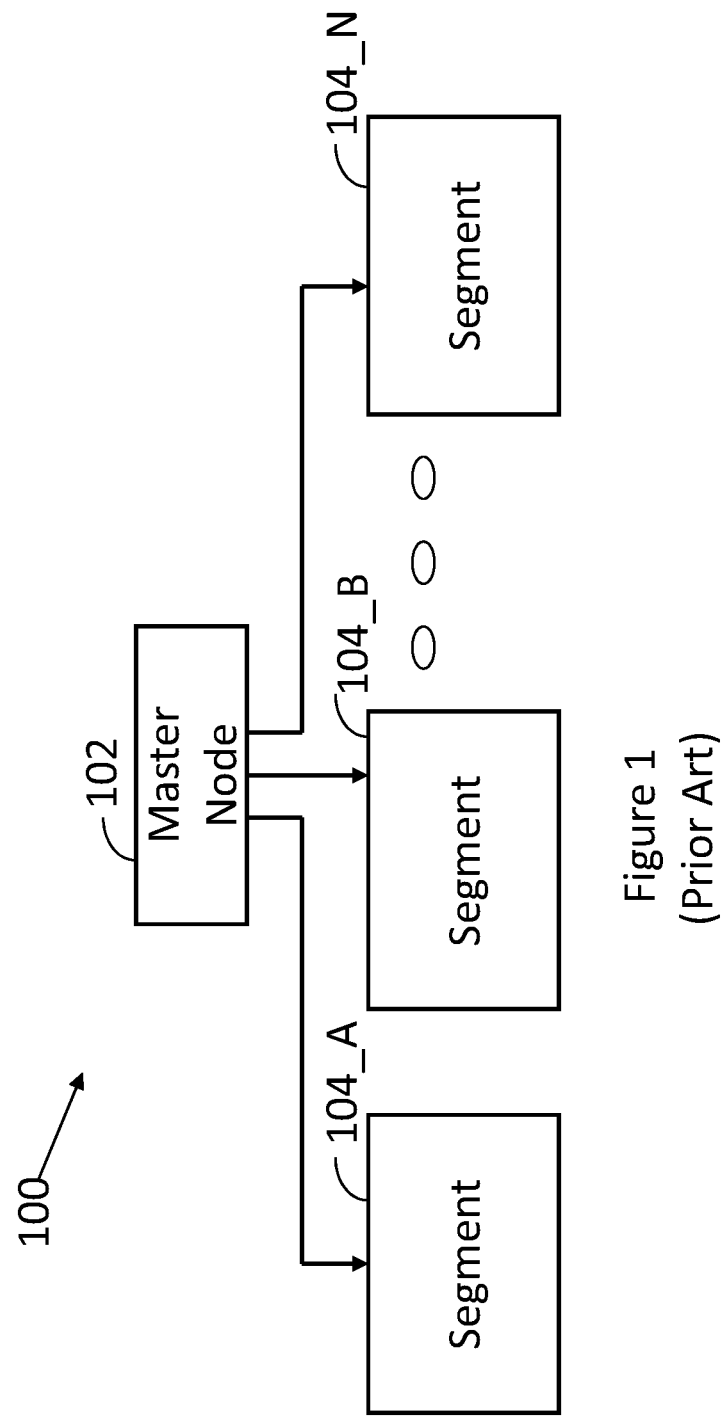
FIG. 1 is a block diagram of a distributed parallel database system with which the invention may be employed.

FIG. 1 illustrates the architecture of a massively parallel processing (MPP) distributed shared-nothing relational database system 100 of the type with which the invention may be used. The MPP relational database system 100 includes a master node 102 and a plurality of distributed shared-nothing segments (nodes) 104_A through 104_N. Each segment node 104 has its own private memory, disks and input/output devices that operate independently of any other node in the database system 100. Each node is self sufficient, sharing nothing across the network, but operating at the direction of the master node. Therefore, there are no points of contention across the system and no sharing of system resources among segments. The advantage of this architecture is that it is highly scalable and that it is able to process large quantities of data distributed across the various database segments in parallel and independently of other segments.

Figure 2:
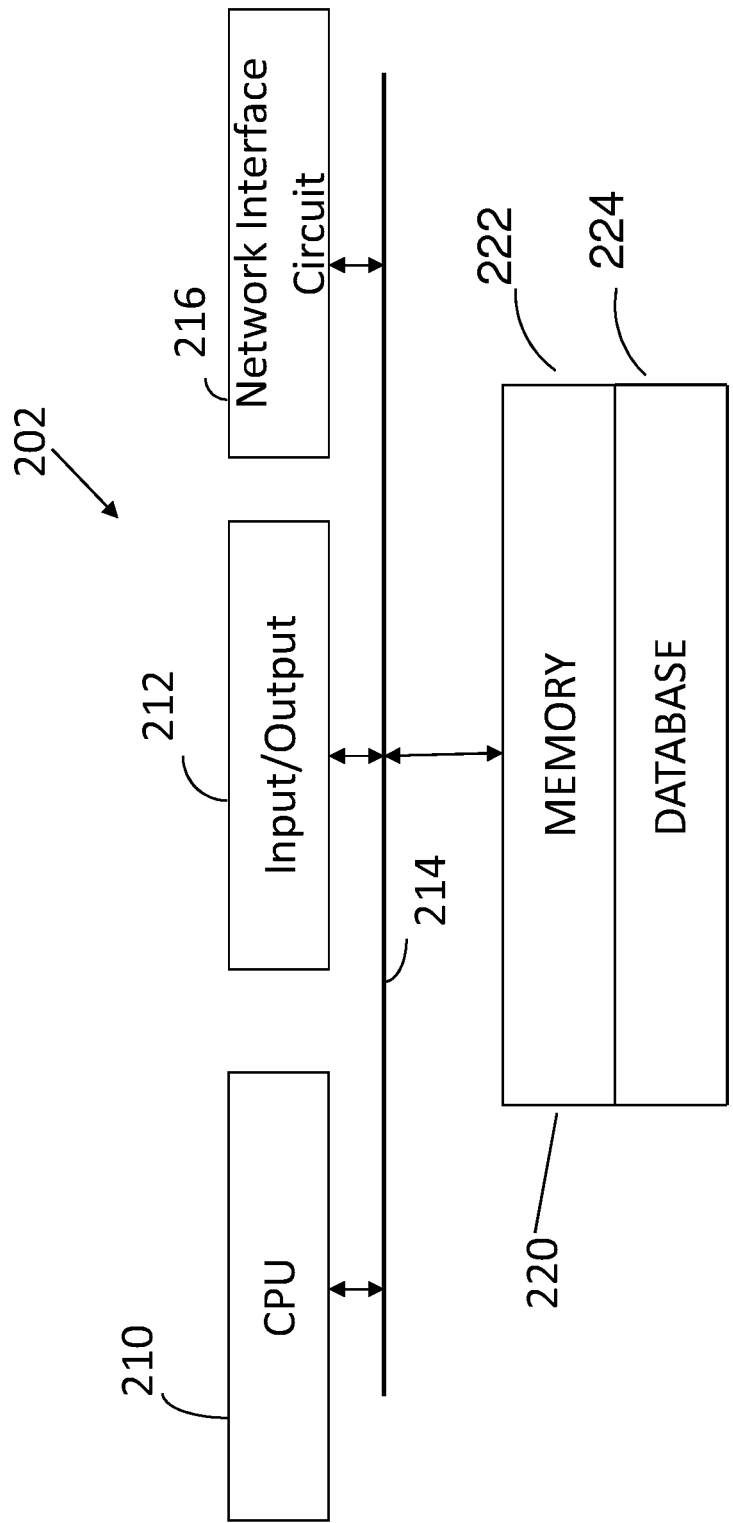
FIG. 2 is a block diagram illustrating a node of the database system of FIG. 1.

FIG. 2 illustrates an example of the architecture of a master node 202 of the database system that is configured to perform processes and operations in accordance with the invention. The master node and the segment nodes may have substantially the same architectures. The master node 202 may comprise a host computer (CPU) 210 (which may comprise a single CPU or may be a multi-processor system comprising a plurality of CPUs) connected to input/output (I/O) devices 212 by a bus 214. The I/O devices may be standard computer system input and output devices. A network interface circuit 216 may also be connected to bus 214 to allow the master node to operate in the networked environment of the database of FIG. 1. The master node may further have storage 220 comprising non-transitory physical storage media connected to the bus that stores executable instructions to control the operations of the computer system. Storage 220 may include a main memory 222 comprising instructions that control the CPU to operate in accordance with the invention, as will be described, and may contain other storage 224 comprising a database and a database catalog. The catalog in a database, as is well known, stores, among other things metadata describing the logical attributes of database objects (tables), and serves as an index to the actual user data distributed across the various segments.

Parallel distributed database systems of the type shown in FIGS. 1 and 2 store data in tables that are distributed across the plurality of segments. Data is typically stored by assigning each datum (e.g., record or row) to a table on one of the segment nodes. The advantage of this data storage approach and database architecture is its inherent data and query parallelism. Each of the plurality of segment nodes is able to process queries independently and in parallel on the data stored locally in the database of that segment, and forward the results to the master node for reporting or further processing. As used herein, the term "row-wise" in reference to data means that all of the SNPs for each individual are stored in one row. Alternatively, all of individuals' variants (or genotype) for one SNP are stored in one row. The term "entry-wise" in reference to data means that each entry, or value in an array, is stored in its own row. This means that each variant for each individual has its own row, and that individuals will have as many rows in a table as they have entries in their arrays, or variants total.

As will be described more fully, the invention enables rapid analysis and processing of genomic data, specifically genetic variants, through storing the data in a distributed framework using a purpose-built data model. By performing analyses in-database with this data model, genetic data is readily and efficiently processed, and relevant additional data, e.g., phenotypic data, is also readily accessible to discover whether there is an association with a genotype, meaning the phenotype can be attributed to a genetic variant. Additionally, the invention facilitates easy parallelization and use of many statistical methods known in the field, and enables in-database permutation analyses to determine the significance of any association that is discovered.

As noted above, genetic data may be represented and stored as row-wise flat file data in many different formats. Genetic data of a single individual may be stored on a row of an array of data elements of different data types in a row-wise flat file that contains the genotypes in a predefined order for genetic markers. FIG. 3A is an example of such an array of row-wise flat files. It shows for multiple (N) individuals on separate rows the genotype data for each individual on a row of the array for one hundred SNPs 1-100. FIG. 3A shows that for individual ID 1, her alleles at SNP 1, 2 and 100 are AA, CC, and TA respectively, and for individual ID 2 for the same SNPs his alleles are AC, TC and AT respectively. In FIG. 3A, each row corresponds to only one individual, and shows data for only 100 SNPs. However, in some data sets there could be several million SNPs. Each flat file may also contain row-wise genetic data for multiple individuals. The flat file for an individual may also include on the same row other information related to the individual. FIG. 3B illustrates flat file data such as shown in FIG. 3A for 1,000,000 SNPs for a population of 270 individuals combined with a plurality of additional covariate data values for each individual such as sex, age, and body mass index (BMI) on the same row as the genotype data. As shown, each row of data in the array comprises a very large flat file.

Other common and intuitive representations of genetic data for a plurality of individuals are variant cell format (VCF) files and VCF-like files, which are typically the ways genetic data is represented. These are row-wise flat files that store and represent on one row SNP data for a particular SNP derived, for instance, from sequencing or from a chip, for multiple individuals with the data for each individual stored in separate fields (columns of an array), similar to the format shown in FIG. 3C. FIG. 3C is a representation of only some of the fields of a row-wise VCF-like flat file format. The VCF-like format may also contain additional information about the SNPs including quality scores, filters, etc. Only the SNP ID is shown in FIG. 3C, although more information, e.g., location, may also be included.

Storing and processing data in row-wise flat files and tables such as the ones described above for FIGS. 3A-C is very inefficient, even when the alleles are inserted as arrays as shown. It is very difficult and time consuming to add additional individuals or additional SNPs to such arrays of flat files, which is a common in experiments. Additionally, if multiple small files were used in lieu of fewer larger files, row-wise files would still be inefficient. Moreover, running comparisons across individuals requires that the data first be extracted out of the flat file format, or otherwise accessed independently. This requires scanning an entire row of flat file data to access the appropriate data values, and this must be repeated each time that a comparison is made. It is a computationally heavy process that it is memory bound, and is a mandatory first step before the data can be processed, regardless of the complexity of the comparison or analysis. For example, a simple count of allele distribution over a population stratified by some disease may require scanning multiple files, and filtering using information derived from another location (for example on disease status). In addition, in order to store any further information about the individuals of a population such as more SNPs or covariate data, e.g. medical conditions, it is necessary to modify the structure of the array table by adding columns or by inserting data values directly into each array.

While processing of an analysis could be performed in parallel on the data by a distributed cluster of computers, any distributed computing cluster will require first grouping the data before sending it to particular clusters for processing, or having each computer node of the cluster scan a particular SNP or individual ID in each row, then perform the specified operations on each row. There may also be additional data available on the individuals or the SNPs as well that may be desirable to include in the analysis. Although this can be done, it is not a simple parallelization process. In distributed computing cluster architectures parallelization needs to be explicit. To process flat files in parallel, the data may have to be moved around to different machines in clusters for processing, and the results returned for visualization inspection. This adds significantly to the processing burden.

The invention addresses these problems, as described below, by converting the row-wise flat file format where each row contains different types of data elements into entry-wise tables having columns that each contain data elements representing the same type of data, and storing the entry-wise tables in an MPP distributed relational database such as described and shown in FIGS. 1 and 2. This leverages the inherent distributed data distribution and query parallelization of such databases for all queries and analyses, and eliminates the otherwise necessary initial processing steps for flat files described above for cluster computing systems before each analysis. A data model in accordance with the invention comprises entry-wise tables in which different data values of the same type of data element are stored in corresponding columns that are headed (indexed) by data element type, as for example, by individual identifier, genetic marker identifier, and corresponding genotype value for the individual and marker. Moreover, with the entry-wise data model of the invention it is very easy to add rows to the table data for additional individuals or additional markers. The data model format may also include additional columns in the table for information about marker-individual pair, for example, the number of reads contributing to an allele count, and source data files such as microarray or sequences mapped to this locus. As will be described more fully, by storing data using this data model and in this entry-wise format, the invention enables parallel access and analysis of each SNP directly, and facilitates testing, for example, for a significant association between a phenotype and a genotype; extracting individuals with a particular set of genotypes for comparisons; permutation testing; and finding regions with potential identity by descent using window functions.

Figure 4:
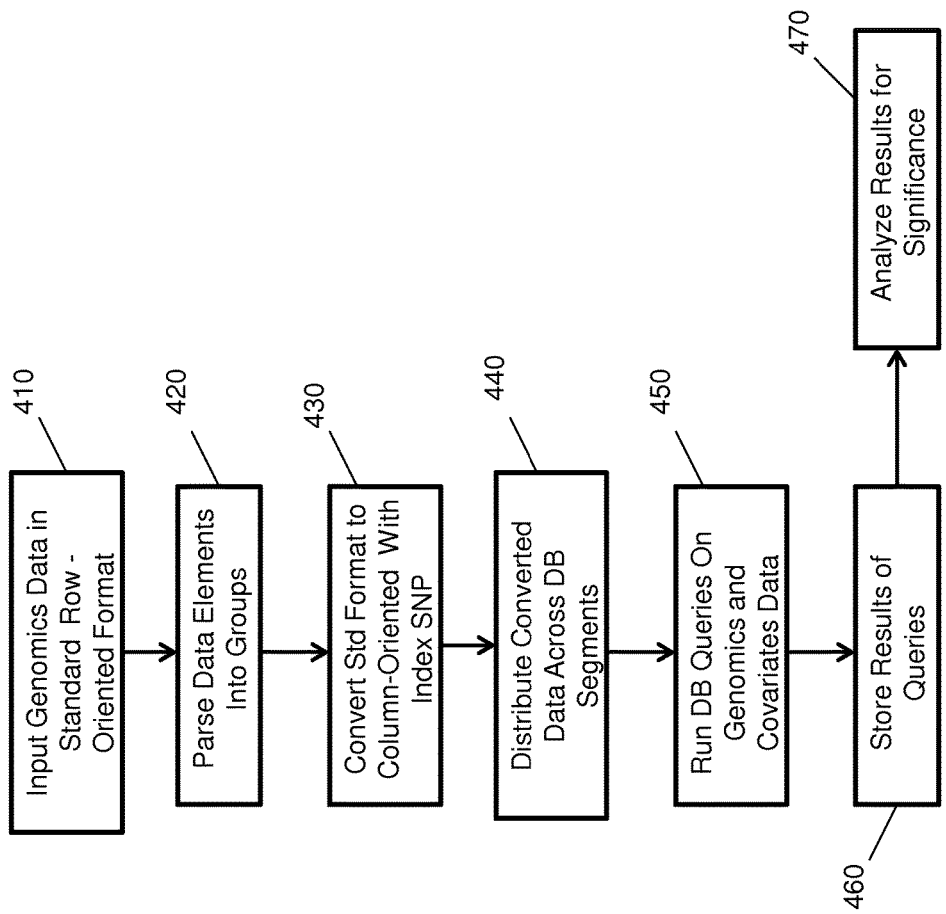
FIG. 4 is a flow chart of a method in accordance with an embodiment of the invention for converting conventional format genetic data into a column oriented data model and for analyzing the data process.
Figure 5:
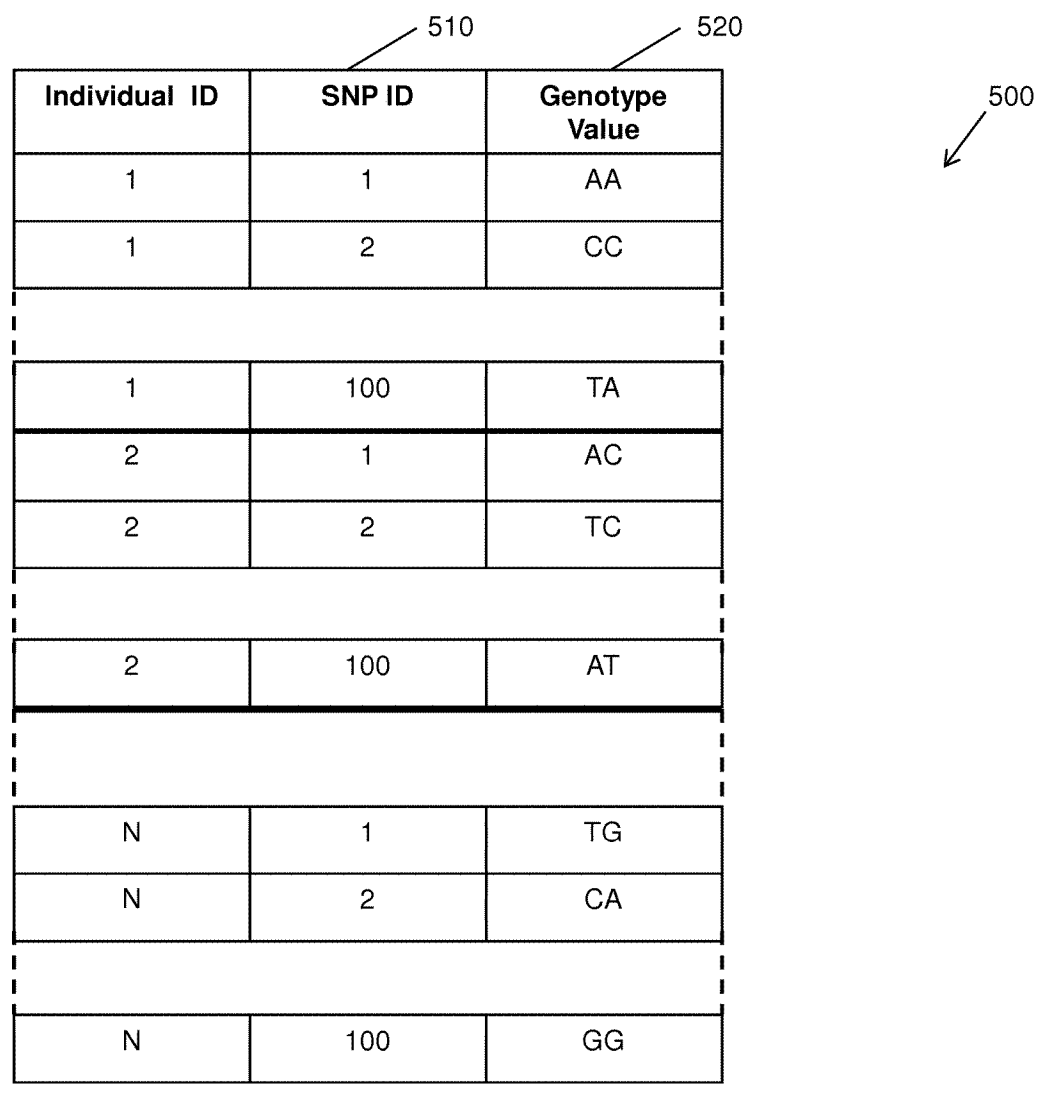

FIG. 4 illustrates an embodiment of a process in accordance with the invention for in-database processing of genomic data. The process may be performed by the master node 102 of the MPP database system 100. Referring to FIG. 4, at 410 data of different data element types in a standard row-wise flat file format such as described above are input to the process, and at 420 the data elements are parsed into groups. At 430, the standard format data are converted in accordance with the invention into a columnar array of data elements in entry-wise format which is more suitable and efficient for parallel analysis by loading the data into database tables having columns containing the same data types and headed (indexed) by data element type such as SNP, individual ID, etc., used for comparisons. Non-genetic data, such as covariate or phenotype data in the input file may be similarly converted and stored in one or more separate tables. FIG. 5 illustrates an example of a preferred entry-wise database table format 500 into which the row-wise genetic data shown in FIG. 3A, for example, may be converted. As shown in FIG. 5, there is a column 510 headed (indexed) by SNP ID, a column 520 for the corresponding genotype value, and 100 rows per individual for each of the N individual IDs for each of the 100 SNPs and their genotypes. At 440, a database management system (DBMS) process of the master node 102 may distribute the converted data across the database segments 104 for storage, and a catalog in storage 224 of the master node keeps track of the distributed data. Covariate data, e.g., phenotype data, such as shown in FIG. 3B and FIG. 6, may also be stored in entry-wise tables such as table 600, FIG. 6, that are distributed across the database segments. Table 600 may have a column 610 indexed by "characteristic" with a separate row for each of a plurality of phenotype characteristics (such as Ethnicity, Sex and Age, as shown) for each individual ID, and a corresponding value the characteristic may be stored in the row of a column 620.

At 450, SQL queries may be submitted to the master node and run on the genomic data and selected phenotype covariate characteristics. At 460 the results of the queries may be stored, and at 470 the results may be further queried to extract datasets of individuals having a particular set of genotypes for further analysis. For instance, various statistical analyses may be performed to identify probable associations between genotypes and phenotypes. Although the invention requires some upfront processing, once it is complete the data may be easily manipulated, selected features compared with other features of individuals, and rapidly filtered by using SQL JOINS. This process is comparable in terms of effort to code and execution time to any other analysis process that would be required to prepare the data for analysis. However, with the entry-wise data model of the invention, the initial processing only ever has to be done once, rather than for each separate analysis for row-wise data.

An example of a basic SQL query on the table of FIG. 5 is as follows:
SELECT
  Individual_ID
  , SNP_ID
  , Genotype
FROM
  genotypes SNPs It is possible to study specific individuals or specific SNPs, or both simultaneously, by adding a WHERE clause to the above query, i.e.,
SELECT
  Individual_ID
  , SNP_ID
  , Genotype
FROM
  genotypes SNPs
WHERE
  Individual_ID IN (1, 2, ...)

Alternatively, to study specific SNPs, the SQL query may be:
SELECT
  Individual_ID
  , SNP_ID
  , Genotype
FROM
  genotypes SNPs
WHERE
  SNP_ID IN (1, 2, ...)

This is not only efficient in terms of writing SQL code, but is also efficient in computation. In the above queries, only the data pertaining to the particular individuals or to the particular SNPs of interest would be scanned. In the conventional row-wise flat file format, each individual's entire set of data would have to be scanned in order to extract the specific SNP information of interest. If the original row-wise flat files were inserted into a traditional database using a data model that emulates the flat file format exactly (columns are individuals, and each row represents a SNP), this would also be inefficient. It requires having to write long and specific queries to access the correct column. This query cannot be easily reused and would also preclude fast joins with additional data on that individual.

It will be apparent from the above examples that it is easy to combine genetic data for an individual with other covariate and/or phenotype data for analysis. For example, in FIG. 3B, individuals may have data for a set of covariates (e.g., age, sex, BMI, etc.) and for 1,000,000 SNPs. As described above, the data format can be converted and the data can be stored and represented in separate distributed tables in the database. Covariates may exist in one covariates table, such as shown in FIG. 6, and SNPs may be in a separate genotypes table, such as shown in FIG. 5. Each individual should only have one assigned Individual_ID, and should have data in both tables that is headed (indexed) by that Individual_ID. Data from the different tables may be conveniently combined for analysis using SQL JOINs.

An example of a SQL query to produce data from the table of FIG. 6 may be;

```
SELECT value, genotype, count(*) FROM
(
    SELECT value, individual_id FROM covariates
    WHERE characteristic='ethnicity'
)ethn
JOIN
(
    SELECT genotype, individual_id FROM genotypes
    WHERE snp_id=1
)SNPs
on ethn.individual_id=SNPs.individual_id
group by value, genotype;
```

Furthermore, in the MPP database using an entry-wise data model in accordance with the invention, distributed computations of the distributions of every SNP can be performed in parallel quickly and efficiently by the different segment hosts, as follows:

```
SELECT value, snp_id, genotype, count(*) FROM
(
    SELECT value, individual_id FROM covariates
    WHERE characteristic='ethnicity'
)ethn
JOIN genotypes SNPs
on ethn.individual_id=SNPs.individual_id
group by value, snp_id, genotype;
```

These examples show that the data model enables the analysis to be easily extended to include any other data and any other types of analyses. For example, one such analysis that is easily done is to test whether a variant is significantly associated with a disease. In this case, an appropriate statistical test to determine the probable relationship between a variant and other data may be implemented as a SQL query, or by using a procedural language such as PL/R, and run in parallel across all SNPs.

Additionally, many researchers are interested in conducting permutation tests. This requires randomly swapping the labels of genetic information of one individual (for example, if someone has a disease) with the genetic information of another individual. This may be easily accomplished by creating random labels for each individual, and then executing a JOIN not on the individual_id but on the random label, thus permuting the data, and re-running the same tests on the permuted data. For example, by adding another column "Random_SNP_ID" to the genotype table of FIG. 5, a random ordering may be produced with the following code:

```
SELECT
    *, row_number( ) OVER (PARTITION BY Individual_ID order by random( ))
    Random_SNP_ID
FROM genotypes
```

Another major benefit of using an MPP distributed database in accordance with the invention is that in any analysis where the significance of an association is tested, the data may remain in the database in a table that can be rapidly queried and sorted. For example, by inserting the SNP_ID and a corresponding p-value of an association test into a table, the results may be rapidly ordered by p-value for manual curation. Moreover, the database may contain other information such as the raw source data that can then be used to validate a finding, attribute a finding to experimental error, or to query other databases that are frequently used to annotate disease.

While the foregoing has been with reference to particular embodiments of the invention, it will be appreciated by those skilled in the art that changes to these embodiments may be made without departing from the principles and sprit of the invention, the scope of which is defined by the appended claims.

The invention claimed is:

1. A method of analyzing genetic data using a distributed parallel framework, comprising:
    receiving row-wise data, each row of the row-wise data storing an identifier of a respective individual and characteristics of the respective individual under respective column names;
    converting the row-wise data into entry-wise tables each organized in a plurality of columns and a plurality of rows, wherein the converting comprises:
        parsing, based on the column names, each row of the row-wise data into genetic data representing genetic variants of the respective individual and non-genetic data representing covariate data of the respective individual;
        storing the genetic data of each row of the row-wise data as a plurality of rows in a first entry-wise table, wherein a portion of the column names in the row-wise data corresponding to the genetic variants are inserted as values in a plurality of rows in the first entry-wise table, wherein the parsing comprises:
            grouping the first entry-wise table by identifiers of the genetic variant or individuals; and
            grouping the second entry-wise table by genotype or individuals, and
        wherein the first entry-wise table is indexed at least by identifiers of the genetic variants, and the second entry-wise table is indexed at least by values of the covariate data; and
        storing the non-genetic data of each row of the row-wise data as a plurality of rows in a second entry-wise table, wherein a portion of the column names in the row-wise data corresponding to the covariate data are inserted as values in a plurality of rows in the second entry-wise table;
    distributing the first and second entry-wise tables across a plurality of database segments of a parallel distributed database; and
    running database queries in parallel on the distributed first and second entry-wise tables by joining the first and second entry-wise tables by the identifier of the individual.

2. The method of claim 1, wherein the row-wise data is stored in one or more variant cell format (VCF) row-wise files, and the column names of the row-wise data are fields in the VCF row-wise files, the fields representing one or more data element types.

3. The method of claim 1, wherein the genetic variants includes single-nucleotide polymorphism (SNP).

4. The method of claim 3, comprising storing the first and second entry-wise tables separately on the database segments.

5. The method of claim 4 further comprising analyzing said genetic data on different combinations of the non-genetic data using SQL queries.

6. The method of claim 1, further comprising computing, in parallel across the plurality of database segments, probabilities of genetic variants being associated with a particular disease by analyzing the genetic data and non-genetic data in the first and second entry-wise tables against data related to said disease in a disease table.

7. The method of claim 1 further comprising analyzing the genetic data by running statistical analytics in parallel on the genetic variants in said stored first entry-wise table.

8. The method of claim 1 further comprising randomly swapping identifiers of rows of the first and second entry-wise tables, and running permutation tests on the first and second entry-wise data tables based upon said identifiers.

9. A non-transitory computer readable medium for storing executable instructions for controlling operation of a computer to analyze genetic data using a distributed parallel framework, comprising instructions for:
receiving row-wise data, each row of the row-wise data storing an identifier of a respective individual and characteristics of the respective individual under respective column names;
converting the row-wise data into entry-wise tables each organized in a plurality of columns and a plurality of rows, wherein the converting comprises:
parsing, based on the column names, each row of the row-wise data into genetic data representing genetic variants of the respective individual and non-genetic data representing covariate data of the respective individual;
storing the genetic data each row of the row-wise data as a plurality of rows in a first entry-wise table, wherein a portion of the column names in the row-wise data corresponding to the genetic variants are inserted as values in a plurality of rows in the first entry-wise table; and
storing the non-genetic data of each row of the row-wise data as a plurality of rows in a second entry-wise table, wherein a portion of the column names in the row-wise data corresponding to the covariate data are inserted as values in a plurality of rows in the second entry-wise table, wherein the parsing comprises:
grouping the first entry-wise table by identifiers of the genetic variant or individuals; and
grouping the second entry-wise table by genotype or individuals, and
wherein the first entry-wise table is indexed at least by identifiers of the genetic variants, and the second entry-wise table is indexed at least by values of the covariate data;
distributing the first and second entry-wise tables across a plurality of database segments of a parallel distributed database; and
running database queries in parallel on the distributed first and second entry-wise tables by joining the first and second entry-wise tables by the identifier of the individual.

10. The computer readable medium of claim 9, wherein the row-wise data is stored in one or more variant cell format (VCF) row-wise files, and the column names of the row-wise data are fields in the VCF row-wise files, the fields representing one or more data element types.

11. The computer readable medium of claim 10, wherein the genetic variant includes single-nucleotide polymorphism (SNP).

12. The computer readable medium of claim 11, wherein the operations comprise storing the first and second entry-wise tables separately on the database segments.

13. The computer readable medium of claim 12, the operations further comprising, in parallel across the plurality of database segments, probabilities of genetic variants being associated with a particular disease by analyzing the genetic data and non-genetic data in the first and second entry-wise tables against data related to said disease in a disease table.

14. The computer readable medium of claim 12, the operations further comprising instructions for analyzing said genetic data on different combinations of the non-genetic data using SQL queries.

15. The computer readable medium of claim 9, the operations further comprising analyzing the genetic data by running statistical analytics in parallel on the genetic variants in said stored first entry-wise table.

16. The computer readable medium of claim 9, the operations further comprising randomly swapping identifiers of rows of the first and second entry-wise tables, and for running permutation tests on the first and second entry-wise data tables based upon said identifiers.

17. A system comprising:
one or more processors;
a non-transitory computer-readable medium for storing executable instructions operable to cause the one or more processors to perform operations comprising:
receiving row-wise genetic data, each row of the row-wise data storing an identifier of a respective individual and characteristics of the respective individual under respective column names;
converting the row-wise data into entry-wise tables each organized in a plurality of columns and a plurality of rows, wherein the converting comprises:
parsing, based on the column names, each row of the row-wise data into genetic data representing genetic variants of the respective individual and non-genetic data representing covariate data of the respective individual;
storing the genetic data of each row of the row-wise data as a plurality of rows in a first entry-wise table, wherein a portion of the column names in the row-wise data corresponding to the genetic variants are inserted as values in a plurality of rows in the first entry-wise table, wherein the parsing comprises:
grouping the first entry-wise table by identifiers of the genetic variant or individuals; and
grouping the second entry-wise table by genotype or individuals, and
wherein the first entry-wise table is indexed at least by identifiers of the genetic variants, and the second entry-wise table is indexed at least by values of the covariate data; and
storing the non-genetic data of each row of the row-wise data as a plurality of rows in a second entry-wise table, wherein a portion of the column names in the row-wise data corresponding to the covariate data are inserted as values in a plurality of rows in the second entry-wise table;
distributing the first and second entry-wise tables across a plurality of database segments of a parallel distributed database; and running database queries in parallel on the distributed first and second entry-wise tables by joining the first and second entry-wise tables by the identifier of the individual.

18. The system of claim 17, wherein the row-wise genetic data is stored in one or more variant cell format (VCF) row-wise files, and the column names of the row-wise genetic data are fields in the VCF row-wise files, the fields representing one or more data element types.

* * * * *